US009366659B2

(12) United States Patent
Allyn

(10) Patent No.: US 9,366,659 B2
(45) Date of Patent: Jun. 14, 2016

(54) APPARATUSES AND METHODS FOR DETECTING THE PRODUCTION OF METHAMPHETAMINE

(76) Inventor: Marc Lynn Allyn, Athens, TN (US)

(\*) Notice: Subject to any disclaimer, the term of this patent is extended or adjusted under 35 U.S.C. 154(b) by 360 days.

(21) Appl. No.: 13/134,676

(22) Filed: Jun. 13, 2011

(65) Prior Publication Data

US 2012/0315705 A1 Dec. 13, 2012

(51) Int. Cl.
*G01N 25/22* (2006.01)
*G01N 33/00* (2006.01)
*G01N 27/16* (2006.01)

(52) U.S. Cl.
CPC ............ *G01N 33/0075* (2013.01); *G01N 27/16* (2013.01)

(58) Field of Classification Search
CPC ............................. G01N 33/0075; G01N 27/16
USPC .................... 422/83, 91, 94; 436/159; 702/24
See application file for complete search history.

(56) References Cited

U.S. PATENT DOCUMENTS

| 8,190,443 | B1* | 5/2012 | Ouzounian | G06F 19/3493 455/521 |
| 8,860,579 | B1* | 10/2014 | Alouani | G01N 33/0047 340/632 |
| 2002/0152037 | A1* | 10/2002 | Sunshine et al. | 702/23 |
| 2003/0020618 | A1* | 1/2003 | Hemmer et al. | 340/632 |
| 2008/0262321 | A1* | 10/2008 | Erad | B01L 3/5027 600/301 |
| 2009/0140848 | A1* | 6/2009 | Rollins et al. | 340/521 |
| 2012/0079871 | A1* | 4/2012 | Williamson | G08B 17/117 73/28.01 |
| 2012/0154578 | A1* | 6/2012 | Bzorgi | G08B 21/12 348/143 |

\* cited by examiner

*Primary Examiner* — Shogo Sasaki
(74) *Attorney, Agent, or Firm* — Peloquin, PLLC; Mark S. Peloquin, Esq.

(57) ABSTRACT

A system for detecting a gas released during production of methamphetamine in a residential building includes a sensor. The sensor is attached to a part of the residential building. The sensor outputs a signal in response to detection of a concentration of the gas up to a lower explosive limit of the gas. The system includes a communication link. The communication link receives a signal from the sensor and is configured to produce an output in response to the signal.

30 Claims, 10 Drawing Sheets

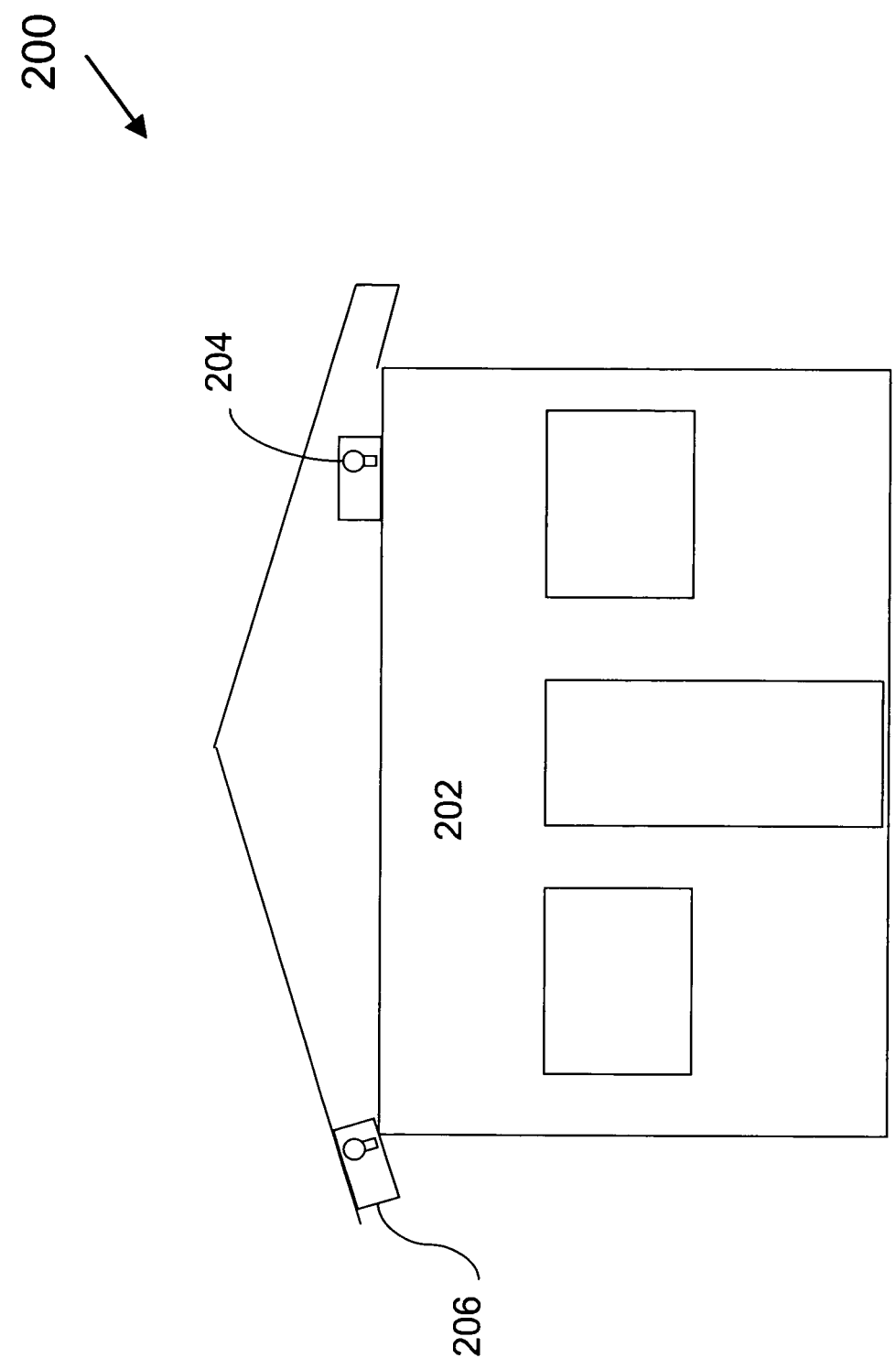

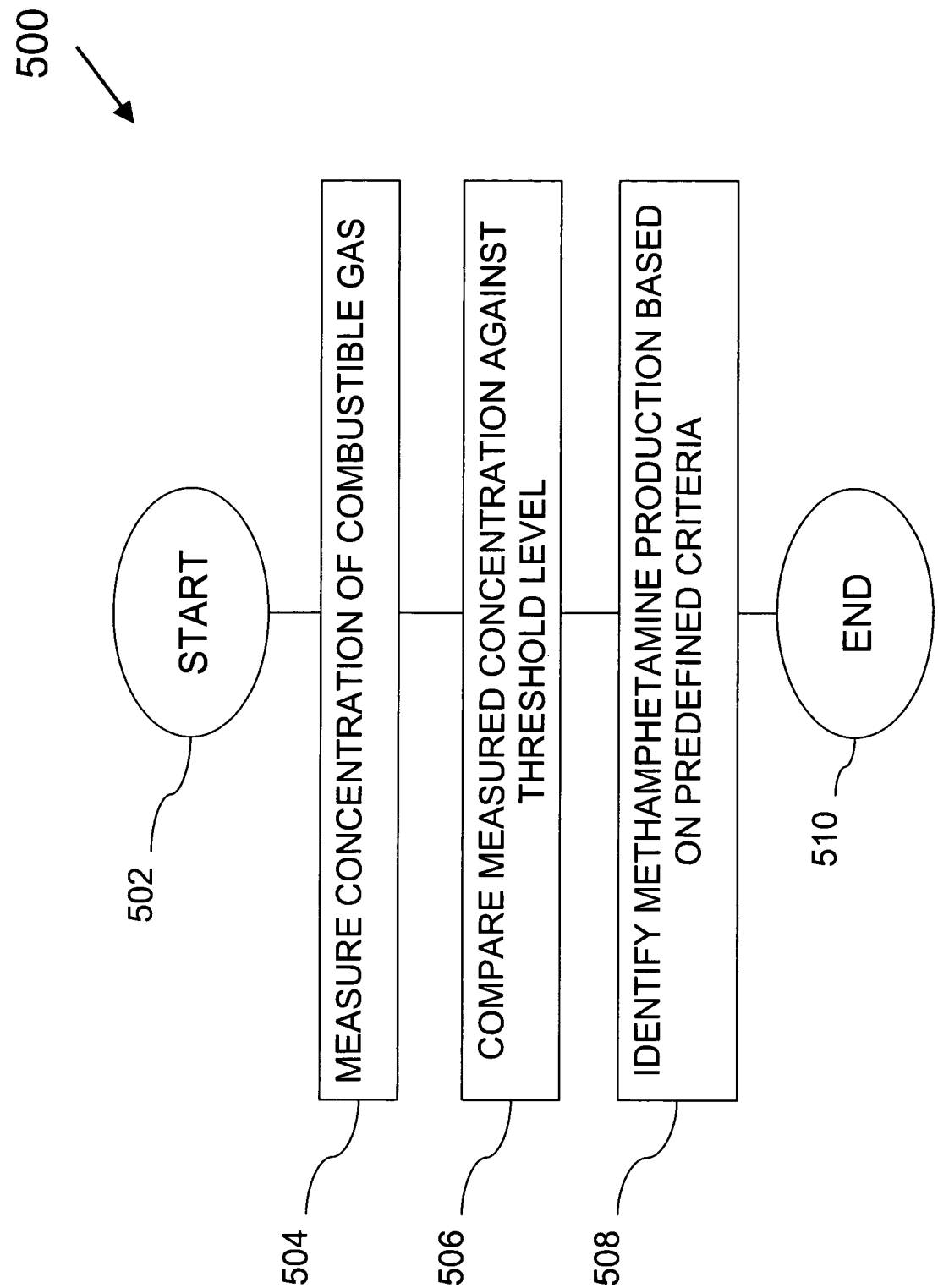

APPARATUSES AND METHODS FOR DETECTING THE PRODUCTION OF METHAMPHETAMINE

BACKGROUND OF THE INVENTION

1. Field of Invention

The invention relates generally to detecting combustible gas in non-industrial locations, and more specifically to apparatuses and methods for covertly detecting and reporting the production of methamphetamine.

2. Art Background

Methamphetamine is a powerfully addictive stimulant, which can be easily produced in illicit laboratories and is generally considered the fastest growing illicit drug in the United States. Methamphetamine use comes with psychological and physical dangers to the user, all of which has become a big problem to society.

Various methods can be used to make methamphetamine. Such methods include reducing ephedrine or pseudoephedrine to methamphetamine via the iodine-red phosphorus method or the ammonia-lithium method. Alternative methods include: reducing ephedrine or pseudoephedrine to methamphetamine via catalytic hydrogenation, and reductive animation of phenyl-2-propanone with aluminum amalgam. These methods produce combustible gas as a by-product of methamphetamine production. One such combustible gas is Phosphine. Production of combustible gas can lead to explosions, fires, death and sever injury all of which have become a big problem.

Methamphetamine laboratories can be easily setup in private indoor spaces. Frequently used private indoor spaces are residential living spaces such as homes, apartments, motel rooms, garages, storage lockers, basements, camping trailers, motor homes, etc. Explosions and fires occurring in these locations have resulted in death, severe injury, and have destroyed property. Chemicals residuals from methamphetamine production collect on the inside surfaces of these indoor spaces, such as the walls, carpets, ceilings, etc. and on materials where methamphetamine is manufactured. Occupants can get sick and/or die from post exposure to contaminants. Specialized hazmat teams must be used to decontaminate or remove contaminated materials; otherwise the buildings must be destroyed. All of this has presented a host of problems.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

FIG. 2 illustrates a mounting location according to embodiments of the invention.

FIG. 5 illustrates a method for processing data collected from a combustible gas sensor, according to embodiments of the invention.

DETAILED DESCRIPTION

In the following detailed description of embodiments of the invention, reference is made to the accompanying drawings in which like references indicate similar elements, and in which is shown by way of illustration, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense, and the scope of the invention is defined only by the appended claims.

Apparatuses and methods are described for detecting the production of methamphetamine.

Production of methamphetamine results in the use of flammable substances. These flammable substances are released into the atmosphere in a gaseous state. Some examples of gaseous flammable substances released during production of methamphetamine are: ammonia, acetone, ethyl alcohol, Coleman fuel, lighter fluid, toluene, diethyl ether, phosphine, etc.

Combustible gases are flammable within a range of concentration know as the explosive or flammable range. The explosive range is defined by a lower explosive limit (LEL) and an upper explosive limit (UEL).

Figure 1A:
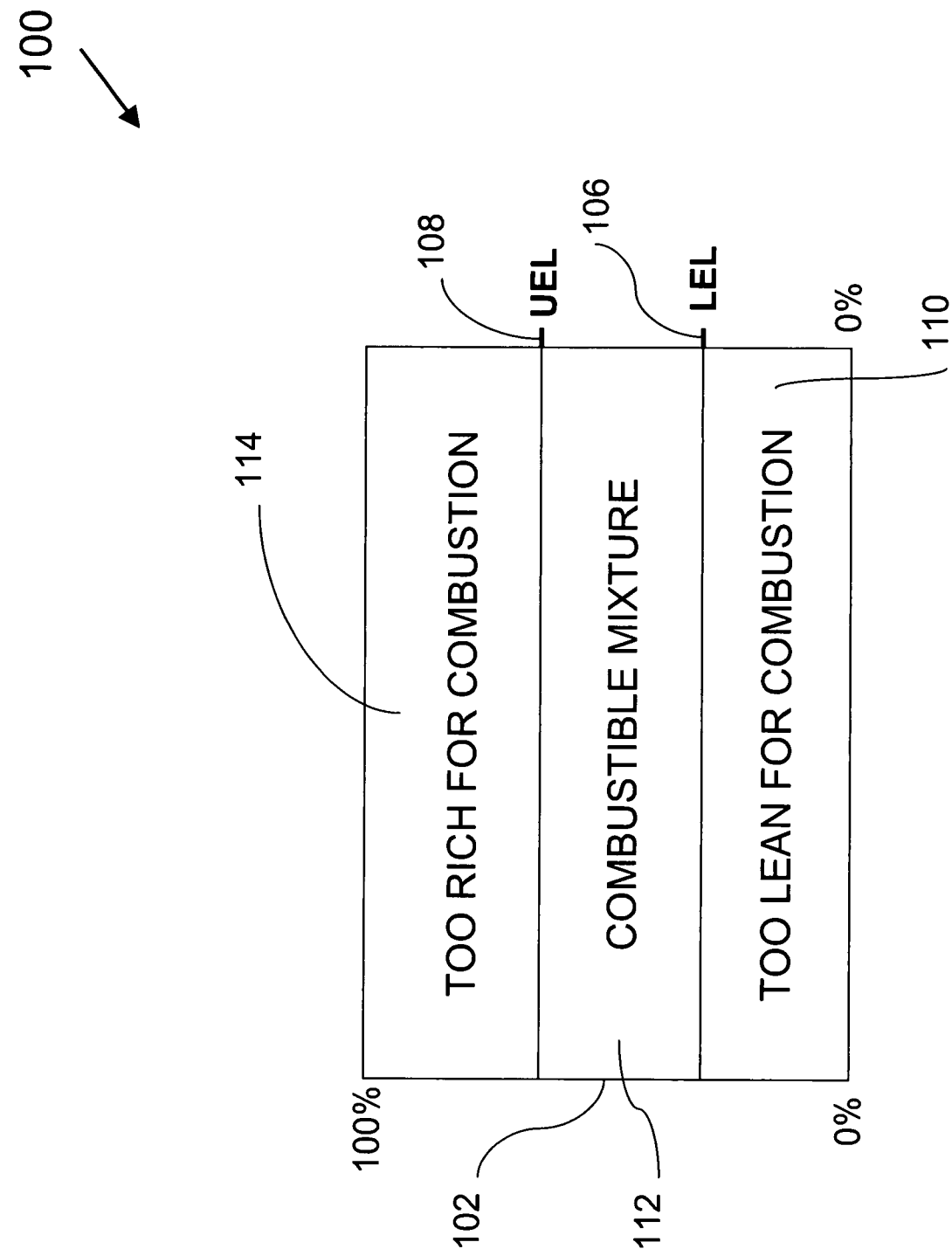
FIG. 1A illustrates a concentration diagram for a combustible gas

FIG. 1A illustrates, generally at 100, a concentration diagram for a combustible gas. With reference to FIG. 1A, a concentration by volume percentage for a combustible gas is illustrated at 102, with limits of 0% and 100%. A lower explosive limit (LEL) is indicated at 106 and an upper explosive limit (UEL) is indicated at 108. Between these limits of concentration, a combustible mixture exists at 112. With oxygen and an ignition source combustion will occur. Below the LEL 106 the mixture is too lean for combustion; this range of concentrations is indicated at 110. Above UEL 108, the mixture is too rich for combustion; this range of concentrations is indicated at 114.

Each gas has its own LEL and UEL. Values for LEL and UEL for some common gases are shown Table 1, directly below:

TABLE 1

LEL and UEL for several combustible gases

| GAS | | LEL | UEL |
| --- | --- | --- | --- |
| Acetone | (CH3)2CO | 2.15% | 13.0% |
| Ethyl Alcohol | CH2H5OH | 3.3% | 19.0% |
| Methane | CH4 | 5.0% | 15.0% |
| Phosphine | PH3 | 1.8% | unknown |
| Toluene | C7H8 | 1.2% | 7.0% |

Sensors made for detecting combustible gases below LEL are typically scaled from 0-100% of the LEL when referring to gas concentration. In this detailed description of embodiments, percentages given will follow with the designation of "LEL" when the percentage refers to percentage of LEL. When the percentage is meant to refer to volume the word "volume" will follow.

Catalytic bead type sensors are used to detect concentrations of combustible gas below the LEL of the gas. Catalytic bead type sensors burn a small amount of the gas on the surface of the bead to obtain a measure of gas concentration. If the concentration of the gas is above the UEL, then Catalytic bead type sensors will not render an accurate reading of gas concentration. Two other types of sensors are used to measure high gas concentrations; these are Thermal Conductivity (TC) and Non Dispersive Infrared (NDIR) sensors.

NDIR sensors are typically not exposed directly to the gas of interest, do not need oxygen to be present, and do not combust the gas in order to measure gas concentration. NDIR sensors will operate across the full measuring range of gas concentration from 0 to 100% volume. Limitation is that a given NDIR sensor doesn't detect all flammable gases.

TC sensors are based on the principle that gases differ in their ability to conduct heat. If a sample gas has a different thermal conductivity than the reference gas, the temperature of the active filament will change as compared to the reference element. A reading is obtained that is proportional to the gas concentration of interest. TC sensors can be used to measure concentrations of a variety of gases and the TC sensor does not need oxygen to operate. Advantages of TC sensors is that like the NDIR sensors, TC sensors can detect gas concentrations across the full measurement range 0 to 100% volume. Limitation is that a given TC sensor doesn't detect all flammable gases.

Several other technologies are used to build sensors for detecting combustible gas such as "Metal Oxide Semiconductor" for detecting Hydrogen, "Galvanic Cell" for detecting Oxygen, and "Electrochemical" for detecting Hydrogen Sulfide and Carbon Monoxide.

Most industry standard combustible gas sensors are powered by 24 volts direct current and provide an output signal of 4 to 20 mA or 0 to 10 volts which is proportional to the concentration of the gas detected. In some cases combustible gas sensors provide discreet on/off state outputs and are often configured with one or more relays that operate when a preset concentration level of gas is detected. A normally closed relay contact on the sensor output relay can be used to detect tampering at the measurement site. In this case tampering would deprive power to the relay which would open the contact and look like a signal, thereby alerting the system that a signal had been acquired. While such tampering would not necessarily mean that methamphetamine was in production it would alert the system operator that the property should be inspected.

Sensors for detecting combustible gases are commercially available from companies such RKI Instruments, Inc. (Union City Calif.); PEMTECH, Inc. (Sugar Land, Tex.); General Monitors, Inc. (Lake Forest, Calif.); Sierra Monitor Corporation (Milpitas Calif.), etc.

Figure 1B:
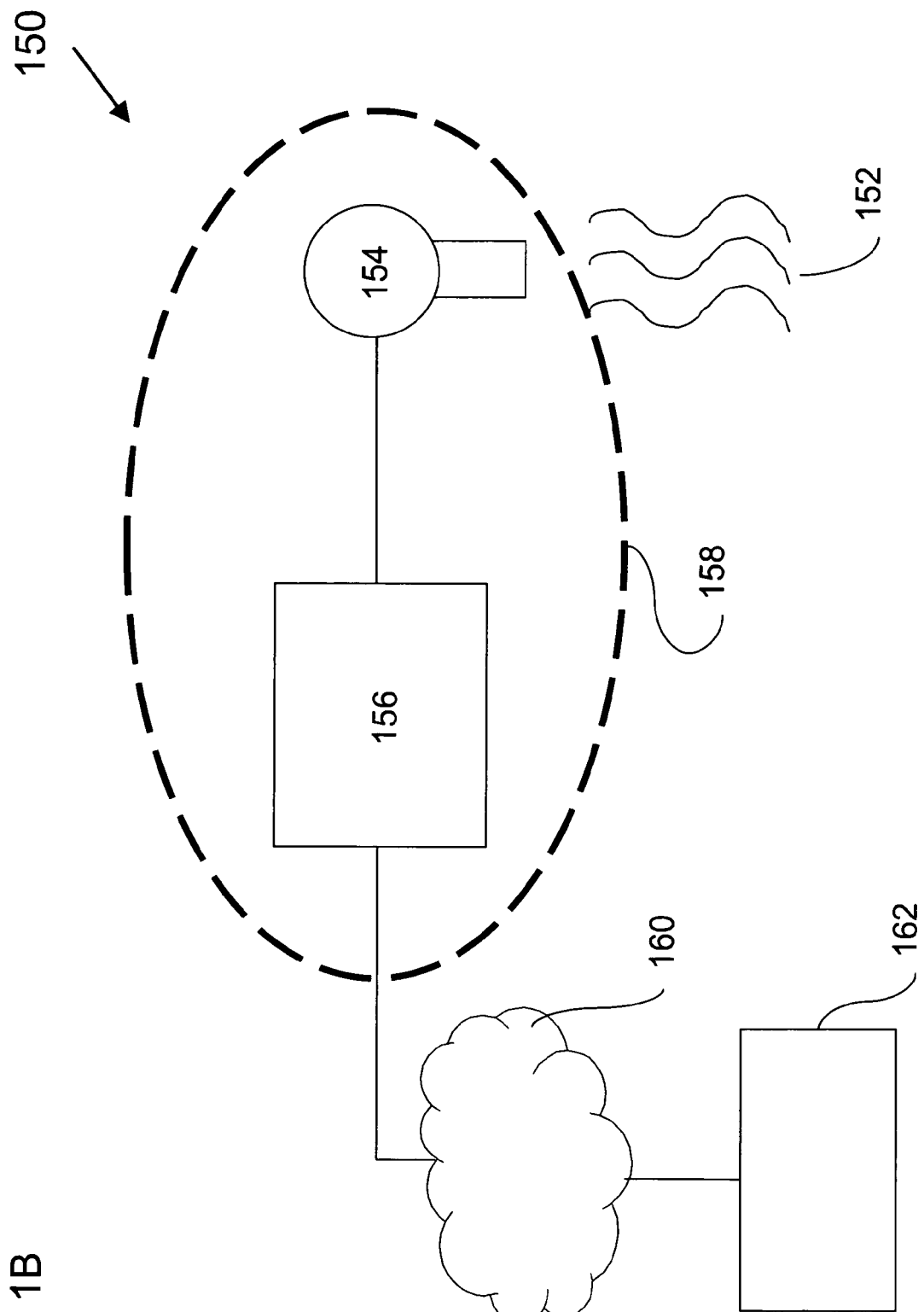
FIG. 1B illustrates a system for detecting methamphetamine production, according to embodiments of the invention.

FIG. 1B illustrates, generally at 100, a system for detecting methamphetamine production, according to embodiments of the invention. With reference to FIG. 1B, a sensor 154 is connected to a communication link 156. A combustible gas 152 is sensed by the sensor 154. In one embodiment, the sensor 154 outputs a signal when the concentration of gas reaches a predefined level. In another embodiment, the sensor 154 outputs a signal which is proportional to the concentration of gas measured by the sensor. The signal output from the sensor 154 is input to a communication link 156. Communication link 156 connects with a remote site 162 via a communication network 160.

In various embodiments, the communication network is a telephone line. The sensor 154 together with communication link 156 dials a remote site by telephone connection. The remote site 162 can be any remote site reachable by telephone connection, such as a telephone, a fax machine, etc. In various embodiments, the communication link 156 is incorporated with the sensor 154 into a package 158. In other embodiments, the sensor 154 and the communication link 156 are packaged separately and are in electrical communication with each other as required. In some embodiments, such communication with a remote site performs a remote alarm function to alert an appropriate party that methamphetamine is being produced in the vicinity of the sensor 154.

In some embodiments, the sensor is connected to a local alarm system (not shown). The local alarm system provides an alarm when a predefined condition is reached. In one embodiment, a predefined condition is measurement of a particular gas concentration. In other embodiments, the alarm system is remote as described above in order to provide a covert system for detecting the presence of methamphetamine production.

In other embodiments, communication link 156 provides an Internet connection via communication network 160, which allows a user via a remote site 162 to access the output of sensor 154. In some embodiments, remote site 162 is a computer with Internet access running an application program that can provide warnings when predefined levels are measured by the sensor 154, thereby providing a remote alarm function for the user.

In yet other embodiments, the communication link 156 can provide a cellular phone connection to communicate information from the sensor 154 to a user at a remote site 162. In such embodiments, the remote site 162 is a device enabled with mobile phone service, e.g., a mobile phone, a mobile computer with mobile phone functionality, etc. The remote site can be under the control of the owner of the property on which the sensor 154 is located or the remote site can be at a law enforcement center such as a police station or the remote site can be a center designed to receive and monitor input from a plurality of sensors at either one location at a plurality of locations.

The sensor 154 and or communication link 156 can be located in a private residence, monitored by the system and the remote site 162 can be located at any distance from the site being monitored. In various embodiments, it is desirable to create a covert monitoring system for methamphetamine production.

FIG. 2 illustrates a mounting location, generally at 200, according to embodiments of the invention. With reference to FIG. 2, an indoor space is illustrated at 202. In one or more embodiments, such a space is referred to as a residential indoor space. The residential indoor space can be any type of indoor space that provides a level of privacy to the occupants and limits the view of the interior of the space from the outside. Since methamphetamine production is an illegal activity, those individuals who participate in such activity desire privacy to avoid notice and arrest by law enforcement officials. Thus, for purposes of a non-limiting illustration, the residential indoor space 202 can be but is not limited to: a house, an apartment, a trailer, a motor home, a garage, an outbuilding, a storage locker, a boat, etc. As used in this description of embodiments, "residential" does not exclude commercial. Therefore, a residential indoor space includes such locations as storage facilities that rent storage spaces to individuals or to business entities.

A sensor 204 is located proximate to the structure that provides the indoor space 202. It is preferable to locate the sensor 204 out of plain site from occupants of the indoor space 202. This is done to prevent occupants of the indoor space from tampering with the sensor 204. The sensor 204 can be located in an air return duct for a forced hot air heating system or a return air duct for a cooling system that is associated with the indoor space 202. Alternatively, the sensor 204 is located in an attic space or in a basement space. When locating the sensor 204 in an attic space location near an air duct is advantageous since gas given off within the indoor space will be drawn into the attic via the duct which will permit measurement by the sensor 204.

The sensor 204 can be built into a ceiling fixture disguised to look like a fire alarm. Such a mounting configuration would provide power and wires for the sensor's output signals. Alternatively, if a wireless transmitter is located with the sensor in the ceiling mount the need to provide a hardwired signal path is eliminated.

Alternatively, the sensor 204 can be built into a surface of the indoor space, e.g., wall or ceiling and located proximate to an opening in the surface such as a light fixture, or electrical outlet. Location of the sensor 204 proximate to a light fixture or an electrical outlet permits the combustible gas to reach the sensor 204. Alternatively, the sensor 204 can be built into a medicine cabinet inside a bathroom. In yet other installations the sensor 204 is built into the cabinets of a kitchen, bathroom, or laundry room. It is preferable to locate the sensor 204 at any place that is not in plain sight of occupants of the indoor space and in such an orientation that gas produced inside of the indoor space can reach the sensor 204.

A sensor 206 can also be located externally from indoor space 202 but proximate to an orifice in a wall of the indoor space such a window or door. The illustration provided in FIG. 2 shows the sensor 206 located proximate to a window and within the soffit of the roof. Location in a soffit of the roof and near a window will permit gas generated within the indoor space 202 to be measured by the sensor 206 as the gas leaks out of the window.

Referring back to FIG. 2 and FIG. 3, the sensor 154, (FIG. 1) sensor 204 and 206 (FIG. 2) can be of the catalytic bead type, non-dispersive infrared (NDIR), thermal conductivity (TC) or other sensors built using technology not yet known. Embodiments of the invention are not limited by the type of sensor used to detect the production of methamphetamine.

In some embodiments, more than one sensor will be deployed at a given location for example, in one or more embodiments, sensor 154, sensor 204, or sensor 206 will include multiple sensors. For example, a catalytic bead type sensor and a NDIR sensor could be located at 154 in FIG. 1. Such a deployment of sensors would permit measurement of a wide plurality of gases when concentrations were below the LEL as well as detection of some gases whose concentrations exceeded the LEL and even the UEL. Such a sensor configuration provides greater measurement functionality at a given location.

Figure 3:
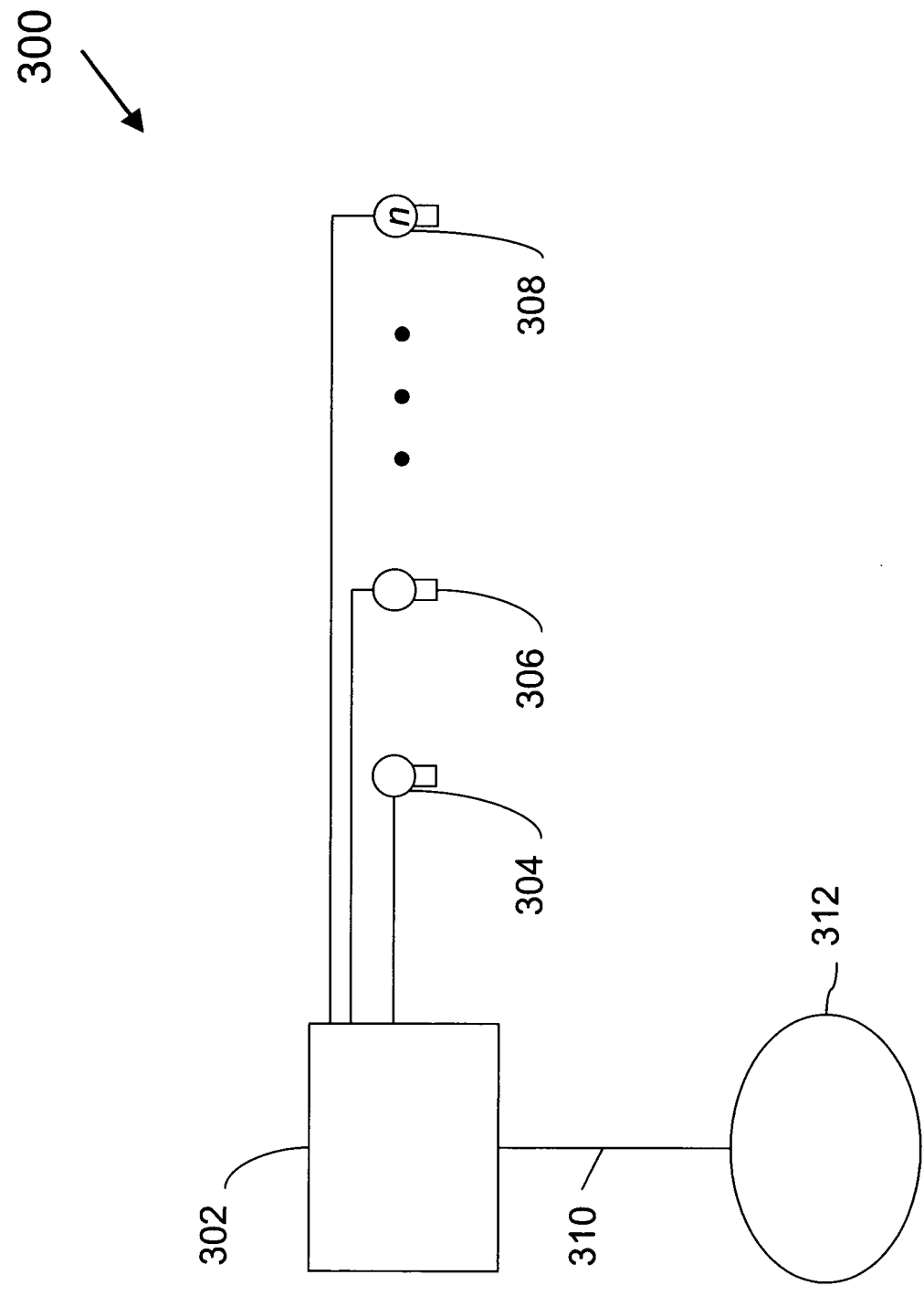
FIG. 3 illustrates a plurality of sensors, according to embodiments of the invention.

FIG. 3 illustrates a plurality of sensors, generally at 300, according to embodiments of the invention. With reference to FIG. 3, a first sensor is indicated at 304, a second sensor is indicated at 306 up to a general number of n sensors indicated at 308. A controller 302 is in electrical communication with the sensors. Such electrical communication can be either wired or wireless. In one or more embodiments, controller 302 is a computer based device that can control the array of sensors and adjust parameters, such as alarm level, perform system tests, introduce delays, perform calibrations, bypass sensors, view time histories of data, perform calculations on the acquired data and report detection of methamphetamine production according to algorithms described below.

In various embodiments, the controller 302 can be a supervisory control and data acquisition system (SCADA) system interfaced to sensors 304 through 308. In such architectures, sensors 304 through 308 can have remote terminal units (RTU) associated therewith to perform functions of data collection, data coding, and data transmission to a master device in the SCADA system. A variety of sensors are commercially available for incorporation into a SCADA system such as the model 5100-28-IT IR Combustible Gas Sensor module from Sierra Monitor Corporation.

A user interface is included to monitor data collected from the array of sensors. The user interface can be located at 302 or at 312. In various embodiments, 312 is a user interface that can be located remotely from the sensors 304 through 308 by means of a network or Internet connection.

The array of sensors 304 through 308 can be deployed in an area where a large number of indoor spaces need to be monitored. For example, in a multi-room house, an apartment complex, a condominium complex, a publicly accesses storage facility, a campground, etc. Data can be accessed remotely at an alarm company facility, police station, from a device with internet connectivity by a property owner who is away on vacation or living off site. No limitation is placed on who or where the monitoring is conducted, the examples given herein are for illustrative purposes only and do not limit embodiments of the invention.

A combustible gas sensor such a catalytic type sensor responds to all combustible gas that burns on the sensor surface. Such a sensor will respond to fumes given off from non-methamphetamine activities, such as using nail polish remover to remove fingernail polish or ammonia used for cleaning. It is desirable to separate out signals that derive from every day innocuous events from signals that result from the production of methamphetamine. In one or more embodiments, separation of such signals is accomplished based on combustible gas concentration level and duration of the signal. Cooking methamphetamine requires cook times that are long compared to the durations of lawful release of combustible gas such as use of nail polish remover or household cleaning. Combustible gas concentration levels released during methamphetamine production are much larger than the lawful domestic releases of combustible gas. The fact that explosions occur during the production of methamphetamine attests to the fact that the gas concentrations of combustible gas has exceeded the LEL and has risen to the combustible mixture range 112 (FIG. 1A).

Figure 4A:
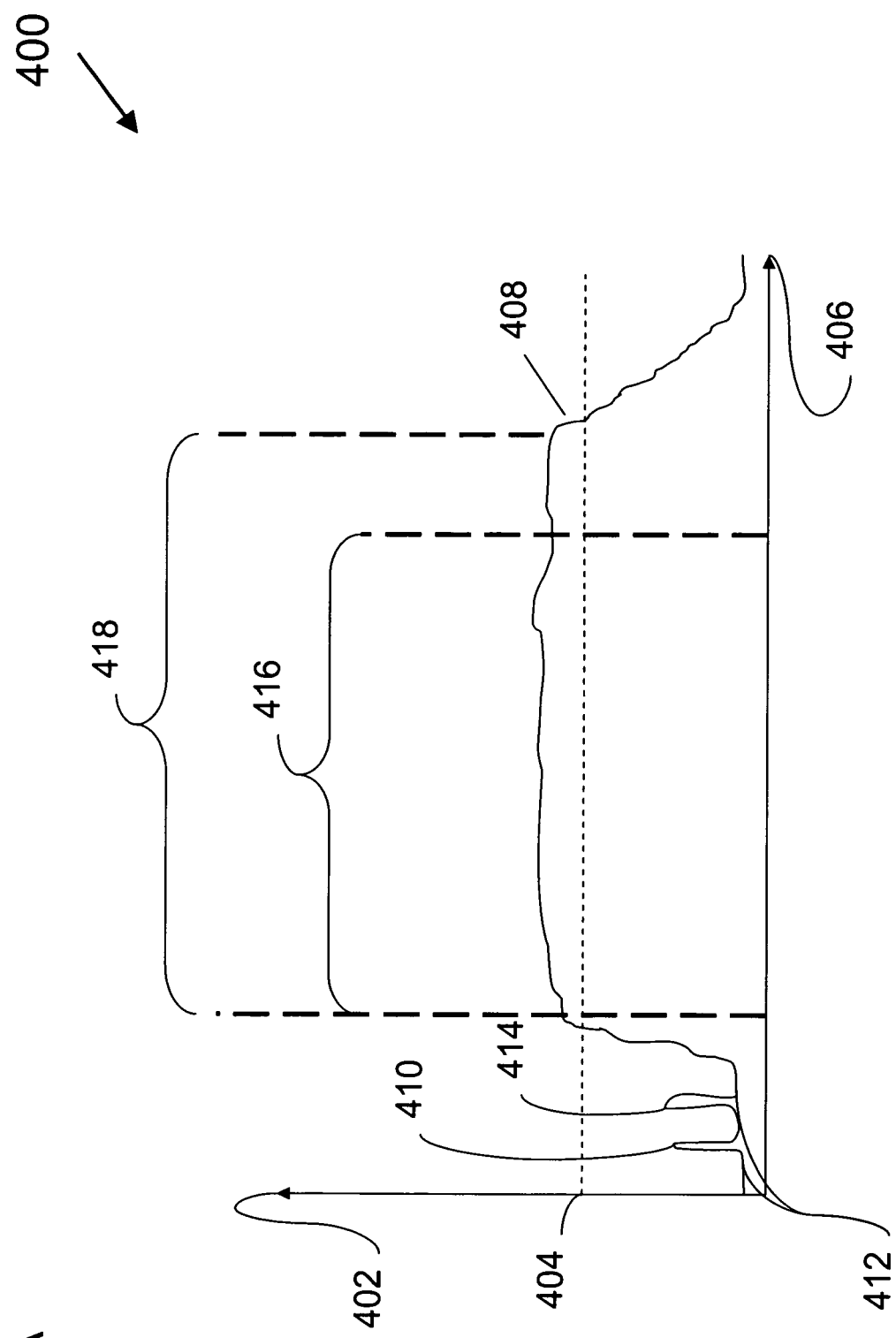
FIG. 4A illustrates a concentration level as a function of time, according to embodiments of the invention.

FIG. 4A illustrates, generally at 400, gas concentration level as a function of time, according to embodiments of the invention. With reference to FIG. 4A, a hypothetical combustible gas sensor collected data over a period of time indicated by the extent of the horizontal axis 406. The data is displayed at 408 with gas concentration on the vertical axis 402 and time on the horizontal axis 406. The total time represented by the extent of the horizontal axis is two hours. Two lawful domestic releases of combustible gas are illustrated by an event 410 and an event 414. These events last for several minutes and can arise from washing a window, using nail polish remover, starting a gas grill, etc. Events 410 and 414 are typically characterized by short time durations and are well below an LEL for the given gas. Note also the low levels 412 measured by the sensor before the event 410 and then measured again after the lawful event 410 passes. In contrast to the lawful event, a methamphetamine cooking event 418 is characterized by a continuous elevated sensor output, which is above a threshold level detection level for methamphetamine production indicated at 404 during the time of the cooking.

Figure 4B:
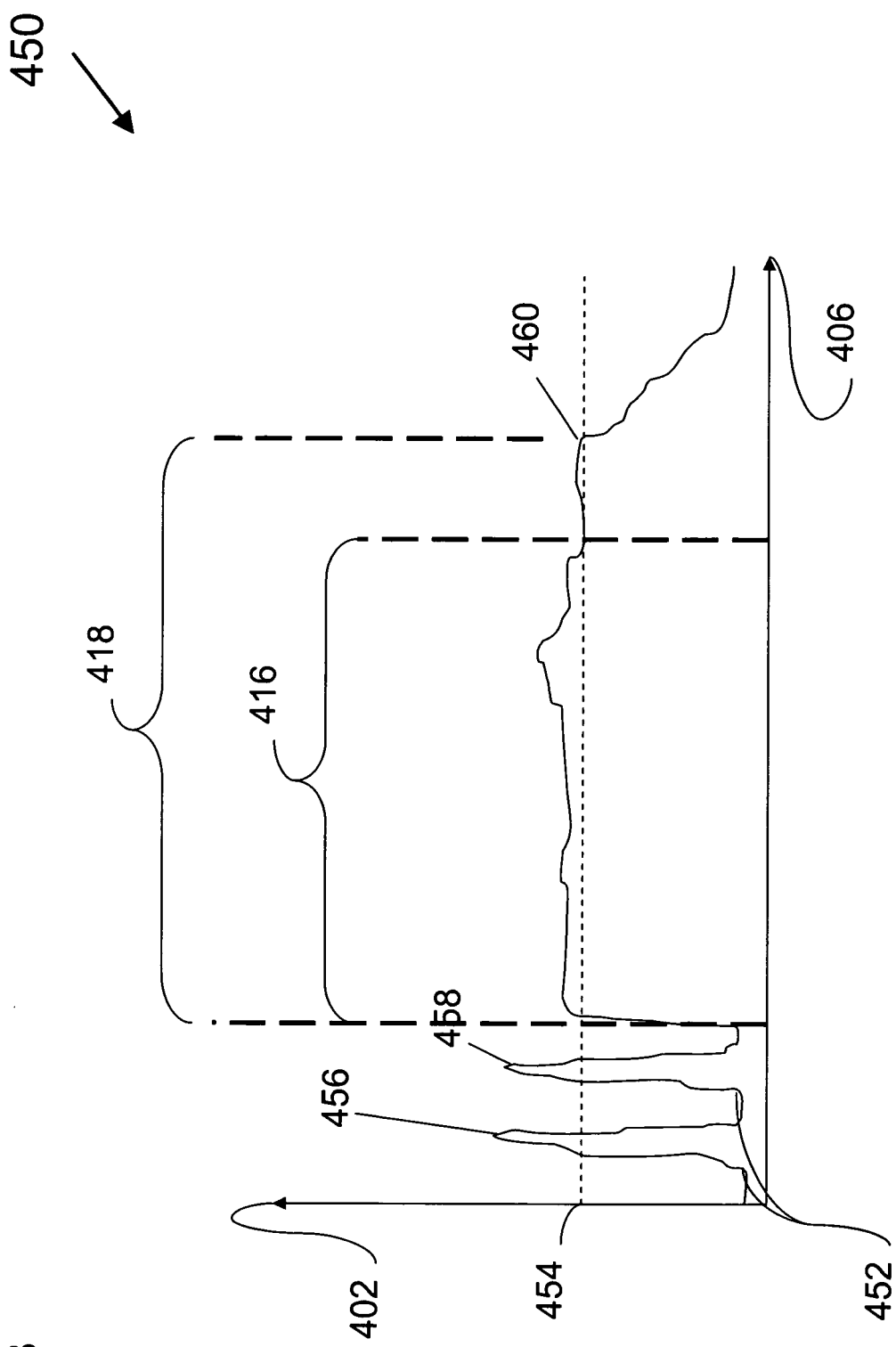
FIG. 4B illustrates a second concentration level as a function of time, according to embodiments of the invention.

FIG. 4B illustrates, generally at 450, a second concentration level as a function of time, according to embodiments of the invention. With reference to FIG. 4B, two lawful domestic releases of combustible gas are illustrated by an event 456 and an event 458. As described above, these events last for several seconds or several minutes and can arise from washing a window, using nail polish remover, starting a gas grill, etc. Events 456 and 458 are typically characterized by short time durations and are well below an LEL for the given gas, however these events can be above a threshold detection level for methamphetamine production. Note also the low levels 452 measured by the sensor before the event 456 and then measured again after the lawful event 456 passes. In contrast to the lawful event, a methamphetamine cooking event 460 is characterized by a continuous elevated sensor output during the time of the cooking.

Methamphetamine is produced by cooking for at least 45 minutes to one hour and as long as 4 hours. A methamphetamine cooking method using ammonium nitrate takes from 45 minutes to one hour to complete. A methamphetamine cooking method that uses red phosphorus has a minimum cooking time of 4 hours. With apriori knowledge of the time that it takes to cook methamphetamine, a threshold time window 416 is established and used to program a computer to automatically detect methamphetamine production from a combustible gas sensor's time record as shown in FIG. 4A and FIG. 4B.

FIG. 5 illustrates, generally at 500, a method for processing data collected from a combustible gas sensor, according to embodiments of the invention. With reference to FIG. 5, a process starts at a block 502. At a block 504 a concentration of combustible gas is measured by a combustible gas sensor. At a block 506 the concentration is compared against a threshold level. At a block 508 predefined criteria of concentration level and duration of the level are compared to determine whether methamphetamine production has been detected.

Figure 6:
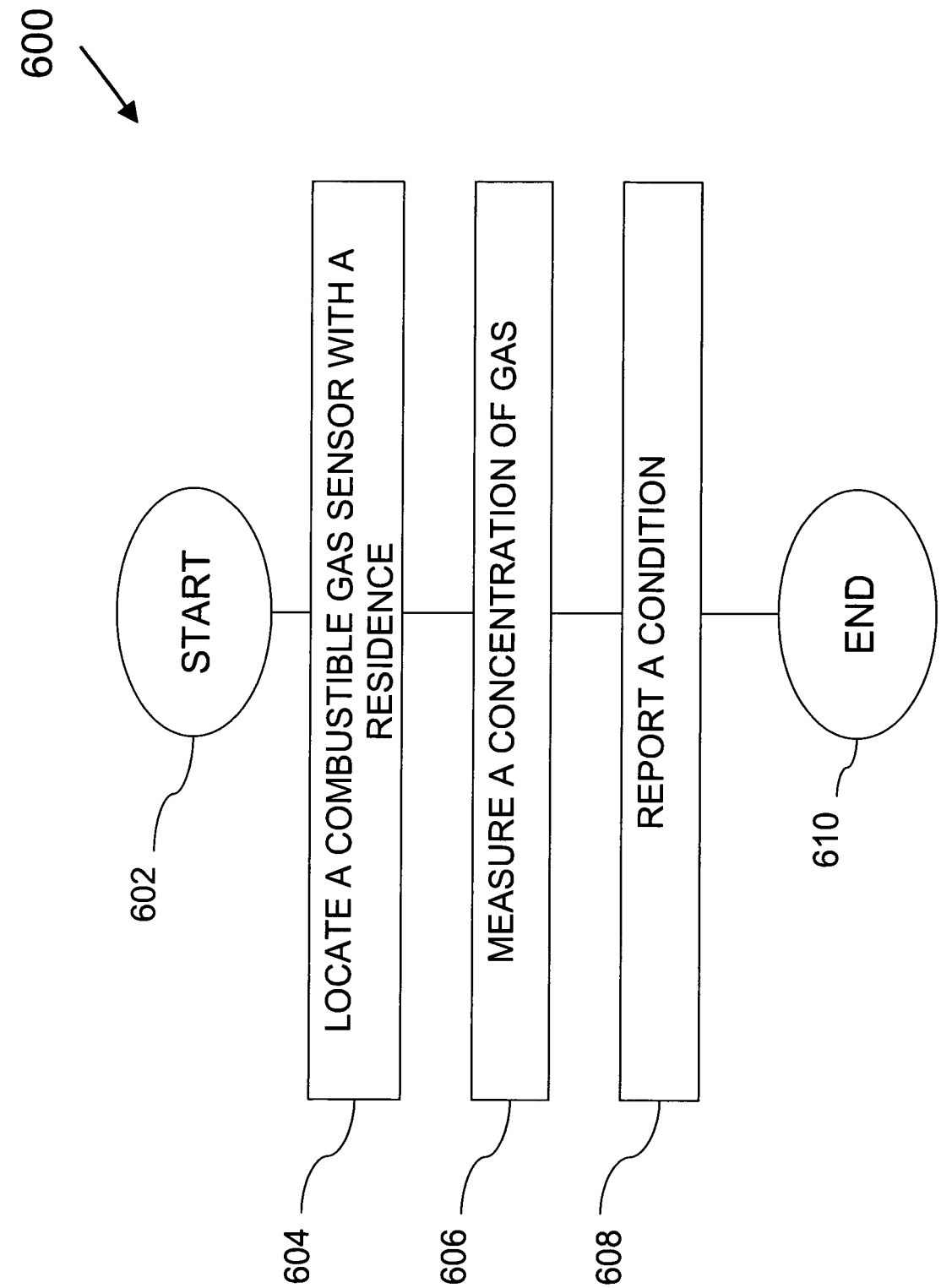
FIG. 6 illustrates a method for detecting methamphetamine production, according to embodiments of the invention.

FIG. 6 illustrates, generally at 600, a method for detecting methamphetamine production, according to embodiments of the invention. With reference to FIG. 6, a process starts at a block 602. At a block 604 a sensor is attached to a residential space. At a block 606 a sensor measures a concentration of a combustible gas. At a block 608 a condition is reported by the sensor. The condition is related to the measured concentration of combustible gas and can be a state of a relay, an analog value of voltage or current, etc. The process ends at a block 610.

Figure 7:
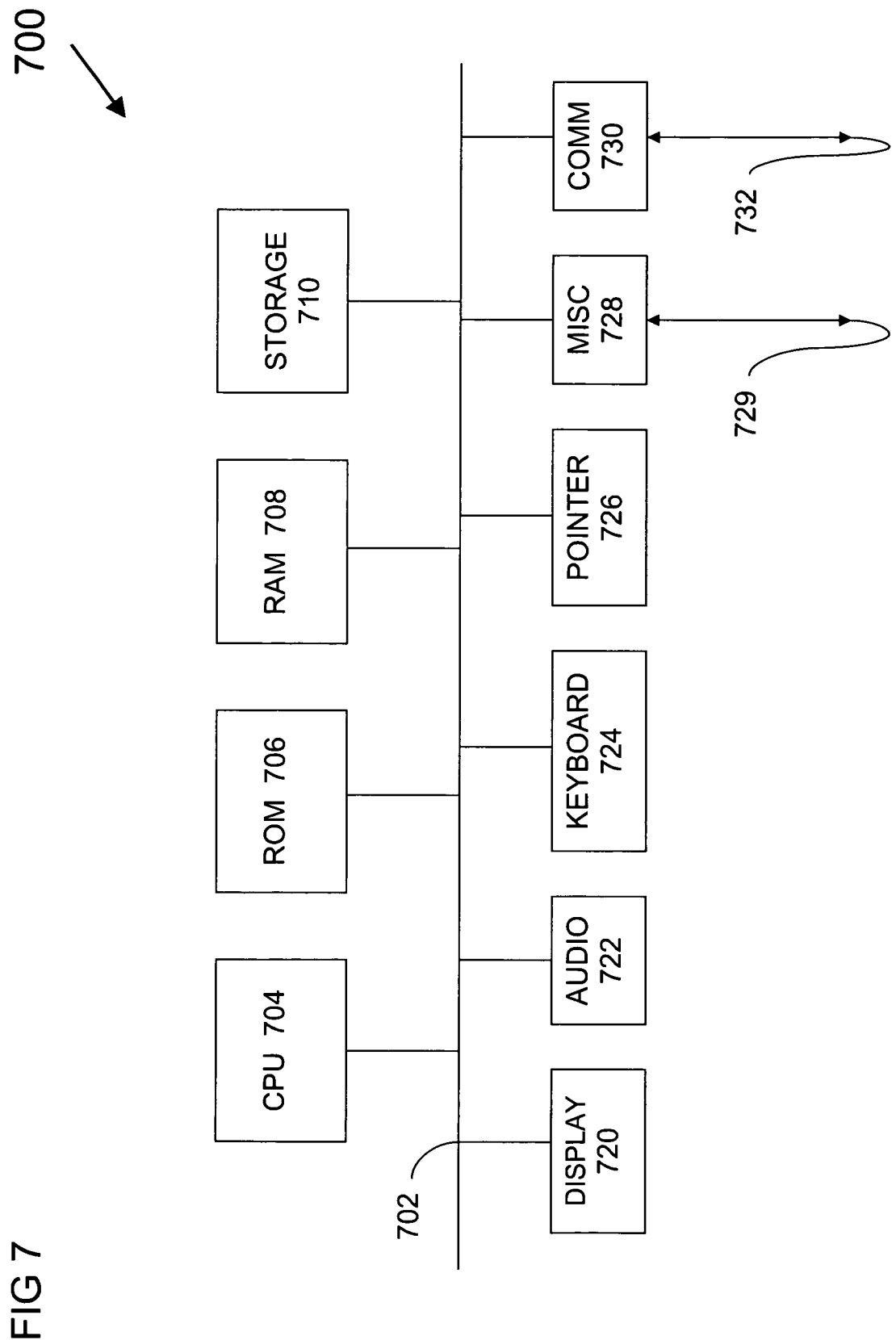
FIG. 7 illustrates a block diagram of a computer system (data processing device such as a computer, smart phone, tablet computer, etc.) in which embodiments of the invention may be used.

FIG. 7 illustrates, generally at 700, a block diagram of a computer system (data processing device such as a computer, smart phone, tablet computer, etc.) in which embodiments of the invention may be used. The data processing system can be referred to as a SCADA system previously described. The data processing system can also be referred to as a data acquisition system. The block diagram is a high level conceptual representation and may be implemented in a variety of ways and by various architectures. Bus system 702 interconnects a Central Processing Unit (CPU) 704, Read Only Memory (ROM) 706, Random Access Memory (RAM) 708, storage 710, display 720, audio, 722, keyboard 724, pointer 726, miscellaneous input/output (I/O) devices 728, and communications 730. The bus system 702 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 794 (FireWire), Universal Serial Bus (USB), etc. The CPU 704 may be a single, multiple, or even a distributed computing resource. Storage 710 may be Compact Disc (CD), Digital Versatile Disk (DVD), hard disks (HD), optical disks, tape, flash, memory sticks, video recorders, etc. Display 720 might be, for example, an embodiment of the present invention. Note that depending upon the actual implementation of a computer system, the computer system may include some, all, more, or a rearrangement of components in the block diagram. Thus, many variations on the system of FIG. 7 are possible.

Connection with a network is obtained with 732 via 730, as is recognized by those of skill in the art, which enables the data processing device 700 to communicate with devices in remote locations. In some embodiments, a sensor(s) described previously in figures above, can be in communication with the data processing system. In some embodiments, Remote Terminal Units (RTU) are used to send data to the data processing device of FIG. 7. In other embodiments, data from a sensor(s) is sent using the general packet radio service (GPRS) to the data processing device of FIGS. 7. 732 and 730 flexibly represent communication elements in various implementations, and can represent various forms of telemetry, GPRS, Internet, and combinations thereof.

In other embodiments, processing is accomplished locally at the sensor location and one or more components of the data processing device of FIG. 7 is incorporated with the sensor to send data to a monitor and control device such as a RTU or a computer device.

In various embodiments, a pointing device such as a stylus is used in conjunction with a touch screen, for example, via 729 and 728 to allow a user to run queries on data received from a sensor or sensors, sensors in multiple locations, etc. Thus, in various embodiments, a methamphetamine detection system is implemented with a data processing device incorporating various components from the illustration of FIG. 7.

Figure 8:
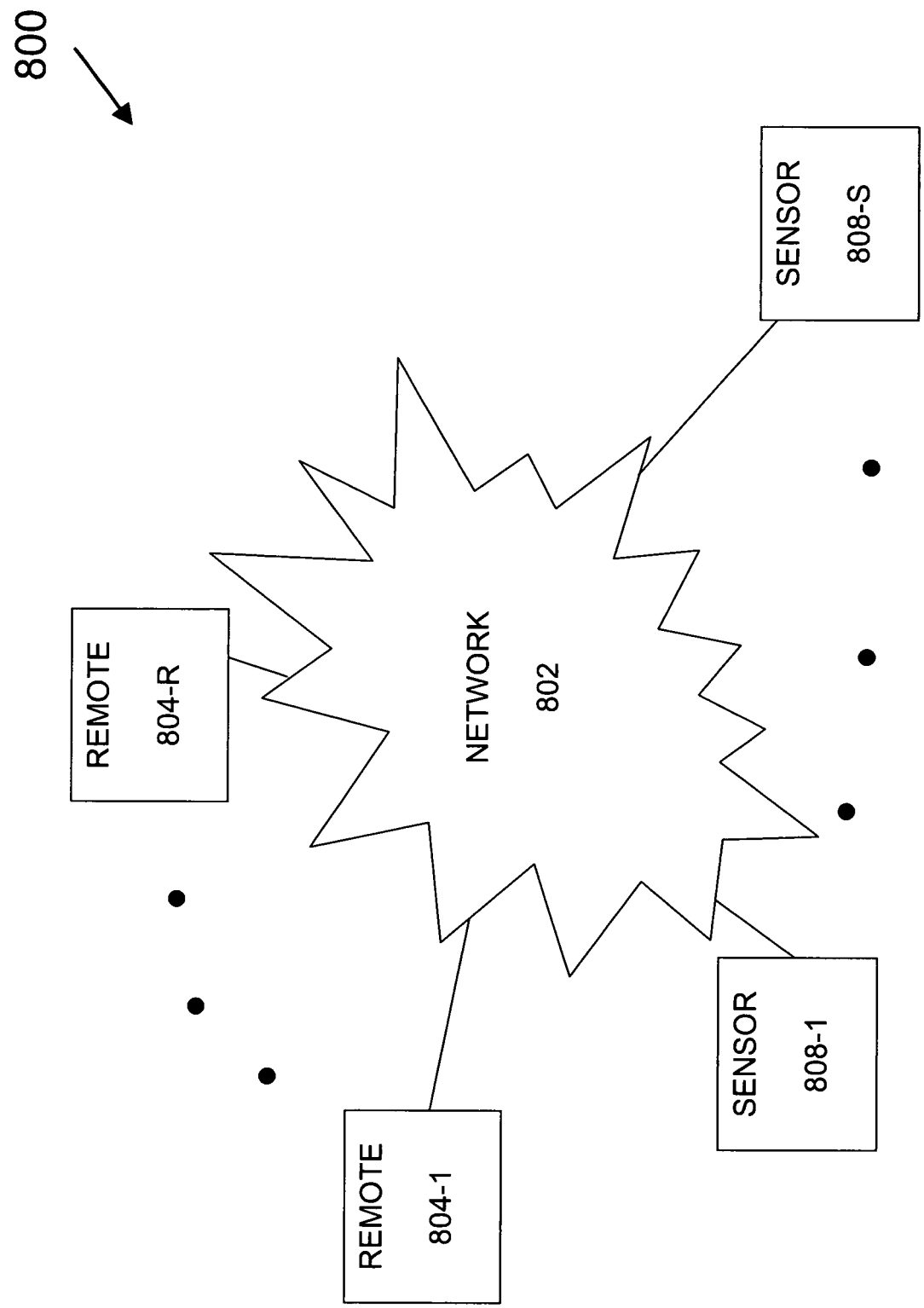
FIG. 8 illustrates a network environment in which embodiments of the present invention may be implemented.

FIG. 8 illustrates, generally at 800, a network environment in which embodiments of the present invention may be implemented. The network environment 800 has a network 802 that connects R remote devices 804-1 through 804-R, and S sensors 808-1 through 808-S. As shown, several data processing devices (computer systems, etc.) in the form of R remote 804-1 through 804-R and S sensors 808-1 through 808-S are connected to each other via a network 802, which may be, for example, a corporate based network. Note that alternatively the network 802 might be or include one or more of: the Internet, a Local Area Network (LAN), Wide Area Network (WAN), satellite link, fiber network, cable network, GPRS, or a combination of these and/or others. The remote devices may have, for example, disk storage systems alone or storage and computing resources. Likewise, the sensors may have in addition to combustible gas sensing ability, computing and storage capabilities. The method and apparatus described herein may be applied to essentially any type of communicating means or device whether local or remote, such as a LAN, a WAN, a system bus, etc.

As described herein, embodiments of the invention can be used to detect illicit methamphetamine production. Such detection can be used to stop methamphetamine production and to prevent loss of life and property damage which can be attendant upon methamphetamine production. Use of embodiments of the invention can result in a decreased production of methamphetamine which can result in decreasing the dangers to society presented by methamphetamine.

Some portions of the description may be presented in terms of algorithms and symbolic representations of operations on, for example, data bits within a computer memory. These algorithmic descriptions and representations are the means used by those of ordinary skill in the data processing arts to most effectively convey the substance of their work to others of ordinary skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, can refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, hard disks, optical disks, compact disk-read only memories (CD-ROMs), and magnetic-optical disks, read-only memories (ROMs), random access memories (RAMs), electrically programmable read-only memories (EPROM)s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with computer system configurations other than those described, including hand-held devices, multiprocessor systems, microprocessor-based or programmable consumer electronics, digital signal processing (DSP) devices, set top boxes, network PCs, minicomputers, mainframe computers, and the like. The invention can also be practiced in distributed computing environments where tasks are performed by remote processing devices that are linked through a communications network.

The methods herein may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, . . . ), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, or mathematical expression. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described, but can be practiced with modification and alteration within the spirit and scope of the appended claims. The description is thus to be regarded as illustrative instead of limiting.

What is claimed is:
1. A system to detect methamphetamine production in a residential building, comprising:
a sensor, the sensor is attachable to a part of a residential building, the sensor outputs a signal in response to detection of a concentration of a gas; and a processor, the processor is electrically coupled to receive the signal and to process the signal to separate an event from a background level, the processor further comprising:

first memory elements to store the event; and second memory elements to store a threshold time window value; wherein the processor to compare a duration of the event to the threshold time window value, wherein two states result:

(1) if the duration of the event is equal to or greater than the threshold time window value a possible methamphetamine production detection is made independently of gas concentration existing above the background level during the event, and a warning signal is generated; or (2) if the duration of the event is not equal to or greater than the threshold time window value then a non-methamphetamine production activity is detected and the warning signal is not generated.

2. The system of claim 1, wherein the sensor is a combustible gas detector.

3. The system of claim 2, wherein the sensor is a catalytic sensor.

4. The system of claim 2, wherein the sensor is an infrared sensor.

5. The system of claim 1, further comprising:

a second sensor, the second sensor is electronically coupled to the processor, the second sensor outputs a second signal in response to detection of a concentration of the gas at any volume percentage of the gas, the processor uses the second signal during separation of the event from the background level.

6. The system of claim 1, further comprising:

an externally mounted sensor, the externally mounted second sensor is mounted to the outside of the residential building and is electronically coupled to the processor, the externally mounted sensor to detects a concentration of the gas below a lower explosive limit of the gas.

7. The system of claim 1, further comprising:

a communication link, the communication link is coupled to the processor, the communication link to facilitate message transmission responsive to the signal.

8. The system of claim 7, wherein the communication link to facilitate message transmission by radio frequency communication.

9. The system of claim 8, wherein the communication link to facilitate message transmission by general packet radio service (GPRS).

10. The system of claim 7, wherein the communication link to facilitates message transmission by connection through the Internet.

11. The system of claim 7, wherein the communication link to provide a connection to a data acquisition system that stores at least one of information related to the concentration of the gas and the concentration of the gas.

12. The system of claim 2, wherein the gas is at least one of phosphine, ammonia, hydrocarbon, oxygen, or carbon monoxide.

13. The system of claim 1, wherein the warning signal is generated when the threshold time window value is at least 45 minutes long.

14. The system of claim 13, wherein the warning signal is generated when the threshold time window value is between 45 minutes and 4 hours long.

15. A system for execution by a processing system to detect methamphetamine production in a residential building, the system comprising:

a processor;

a sensor, the sensor is attachable to a part of the residential building, the sensor outputs a signal in response to detection of a concentration of a gas;

an interface, the interface is electrically coupled to the sensor and to the processor, the interface to receive the signal, the processor to compare gas concentration over time to identify an event resulting in one of two states:

(1) if a duration of the event is longer than a duration of a threshold time window value and a concentration of gas during the event reaches approximately 29 parts per million (ppm) then a possible methamphetamine production detection is made and a warning signal is generated; or (2) if the duration of the event is not longer than the threshold time window value then the event is classified as a non-methamphetamine production activity and the warning signal is not generated; and a system controller, the system controller is in electrical communication with the processor, the system controller permits the threshold time window value to be set remotely.

16. A method to detect a gas released during production of methamphetamine in a residential building, comprising:

attaching a sensor to a part of a residential building, the sensor measures concentrations of gases;

measuring a concentration of a gas with the sensor to identify an event at any concentration level of the gas;

comparing the event with a threshold time window value;

providing a notification of possible methamphetamine production if a duration of the event is equal to or greater than the threshold time window value; and classifying the event as a non-methamphetamine activity if the duration of the event is less than the threshold time window, wherein the notification is not provided.

17. The method of claim 16, wherein the concentration of the gas is approximately equal to 29 parts per million (ppm).

18. The method of claim 16, wherein the gas is at least one of phosphine, ammonia, hydrocarbon, oxygen, or arbon monoxide.

19. The method of claim 16, wherein the part of the residential building is not in plain sight from an interior space of the residential building.

20. The method of claim 16, wherein the part of the residential building is selected from the group consisting of inside of a heating and or ventilating duct, an attic space, a basement space, a stove exhaust duct, a bathroom exhaust duct, a cabinet and a vent.

21. The method of claim 16, wherein the residential building is selected from the group consisting of a house, an apartment, a motel room, a hotel room, a trailer, and a storage locker.

22. A system for execution by a data processing system to detect a gas released during production of methamphetamine in a residential building, comprising:

means for measuring a concentration of a gas with a combustible gas sensor, the combustible gas sensor is mounted to the residential building;

means for analyzing the concentration to identify an event;

means for identifying a non-methamphetamine production activity when a duration of the event is less than a duration of a threshold time window value; and means for identifying a possible methamphetamine production detection when the duration of the event is equal to or greater than the threshold time window value.

23. The system of claim 22, wherein the concentration is approximately equal to 29 parts per million (ppm).

24. A system for execution by a data processing system to detect methamphetamine production, the data processing system comprising:
a processor;
a combustible gas sensor, the combustible gas sensor to output a signal in response to a concentration of a gas;
a network connection, the network connection is coupled to the combustible gas sensor and the processor; and
a non-transitory computer readable storage medium storing executable computer program instructions for causing the data processing system to perform steps comprising:
receiving the signal from the combustible gas sensor, the combustible gas sensor is mounted to a residential building;
analyzing the signal to identify an event;
identifying a non-methamphetamine production activity when a duration of the event is less than a duration of a threshold time window value; and
identifying a possible methamphetamine production detection when the duration of the event is equal to or greater than the threshold time window value.

25. The system of claim 24, further comprising:
a sensor, the sensor outputs a signal in response to detection of a concentration of the gas up to a lower explosive limit of the gas.

26. The system of claim 24, further comprising:
a sensor, the sensor outputs a signal in response to detection of a concentration of a combustible gas at any volume percentage.

27. A computer readable storage medium storing executable computer program instructions for causing the data processing system to perform steps comprising:
receiving a signal from a combustible gas sensor, the combustible gas sensor is mounted to a residential building;
analyzing the signal to identify an event, wherein the event occurs independently of gas concentration;
identifying a non-methamphetamine production activity when a duration of the event is less than a duration of a threshold time window value; and
identifying a possible methamphetamine production detection when the duration of the event is equal to or greater than the threshold time window value.

28. The non-transitory computer readable storage medium of claim 27, wherein the means for identifying the possible methamphetamine production detection occurs when the threshold time window value is at least approximately 30 minutes long.

29. The non-transitory computer readable storage medium of claim 27, wherein the threshold time window value is greater than 10 minutes.

30. The non-transitory computer readable storage medium of claim 27, wherein a concentration of the gas during the possible methamphetamine production detection is approximately 29 parts per million (ppm).

* * * * *